United States Patent [19]

Gunderson

[11] 4,226,234
[45] Oct. 7, 1980

[54] RESPIRATORY VALVE FACE MASK STRUCTURE

[75] Inventor: Arthur M. Gunderson, St. Cloud, Minn.

[73] Assignee: RescueTech Corporation, St. Cloud, Minn.

[21] Appl. No.: 11,136

[22] Filed: Feb. 12, 1979

[51] Int. Cl.³ ............................................. A61M 16/00
[52] U.S. Cl. .......................... 128/205.24; 128/205.25; 128/207.11; 128/207.12
[58] Field of Search ............... 128/145.5, 145.6, 145.7, 128/145.8, 146, 146.4, 146.5, 146.6, 146.7, 205, 205.24, 205.25, 207.11, 207.12; 137/102, DIG. 9

[56] References Cited

U.S. PATENT DOCUMENTS

| 2,990,838 | 7/1961 | Cross | 128/145.5 |
| 3,357,426 | 12/1967 | Cohen | 128/205 |
| 4,151,843 | 1/1979 | Brekke et al. | 128/145.8 |

FOREIGN PATENT DOCUMENTS

| 767609 | 5/1934 | France | 128/146.41 |
| 208855 | 5/1940 | Switzerland | 128/146.5 |
| 19080 | of 1914 | United Kingdom | 128/145.7 |
| 848215 | 9/1960 | United Kingdom | 128/146 |

*Primary Examiner*—Henry J. Recla
*Attorney, Agent, or Firm*—Leo Gregory

[57] ABSTRACT

The respiratory valve face mask herein relates to a structure for use in restoring respiration by providing for a subject of respiratory failure or cardiac arrest a supply of pressurized oxygen enriched air and which permits in the alternative the free passage of ambient air to the subject under atmospheric pressure. The mask comprising the invention herein has a plurality of chin grooves to provide a general face fit for various sizes or lengths of faces with a perimeter overlying the air passages of a face together with appropriate strap members to secure the same about the head of a person and projecting from the inner surface of the mask is a particularly designed air sealing rib encircling the nose and mouth and carried in the mask is a valve structure which permits the face passage of ambient air to the person under atmospheric pressure and into which the input of oxygen or oxygen enriched air under appropriate pressure acts upon a piston to close the valve to ambient air, and further, in connection therewith, is pressure relief to the atmosphere in the event of an excessive build up of the pressure of oxygen or oxygen enriched air within the mask.

9 Claims, 8 Drawing Figures

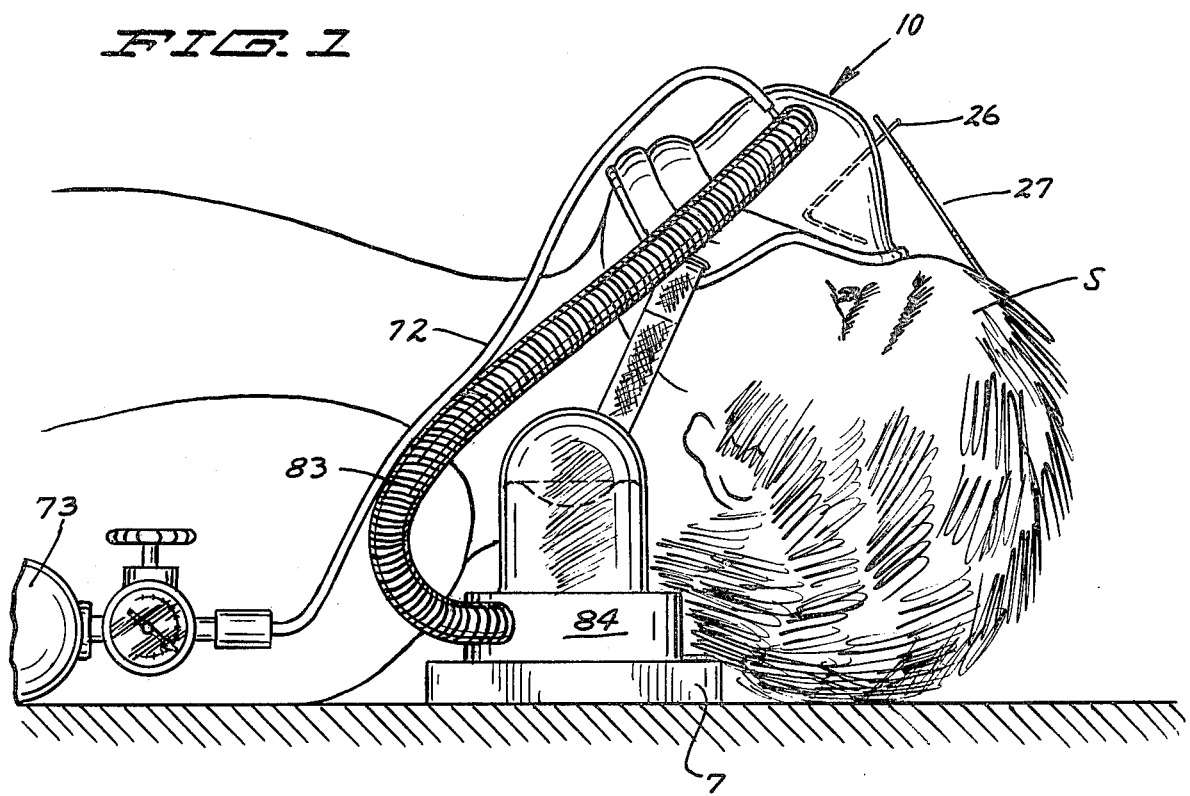
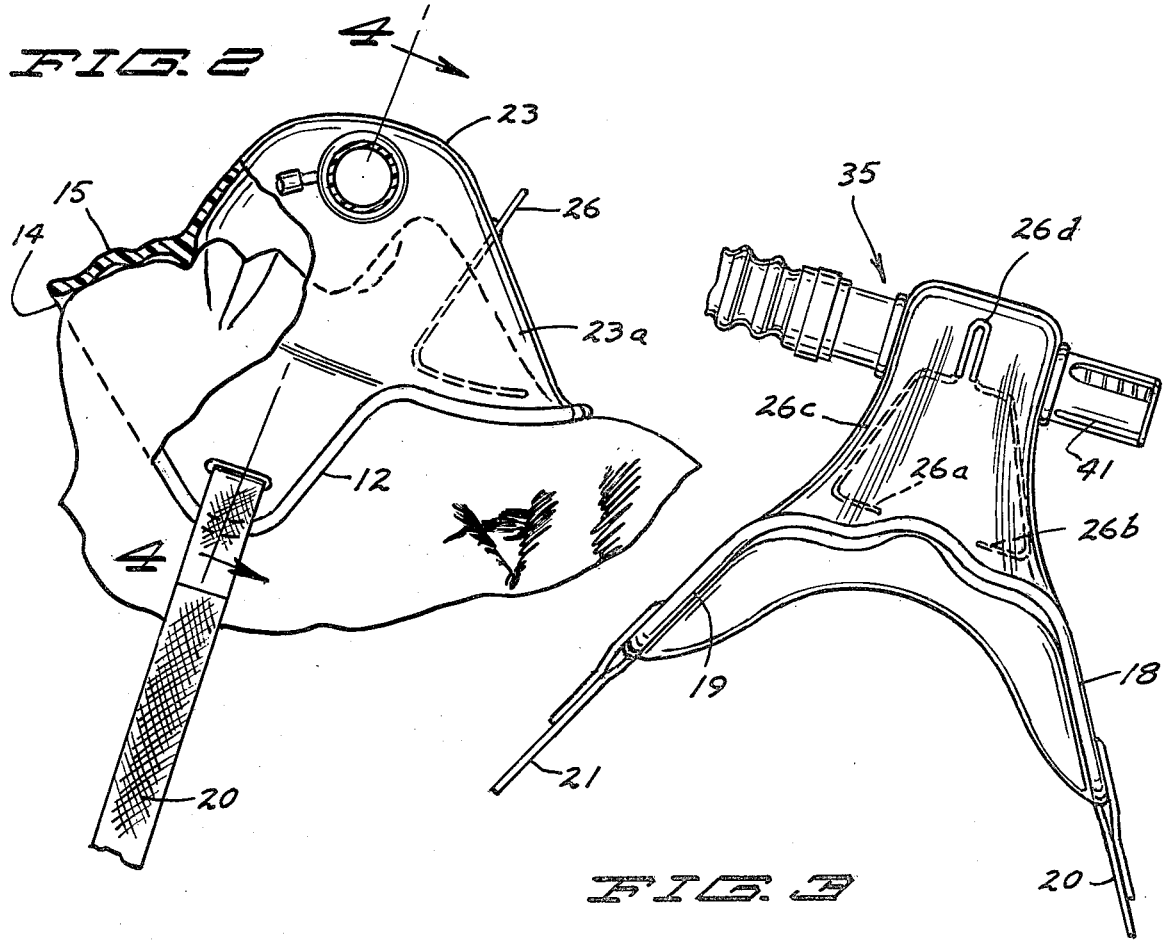

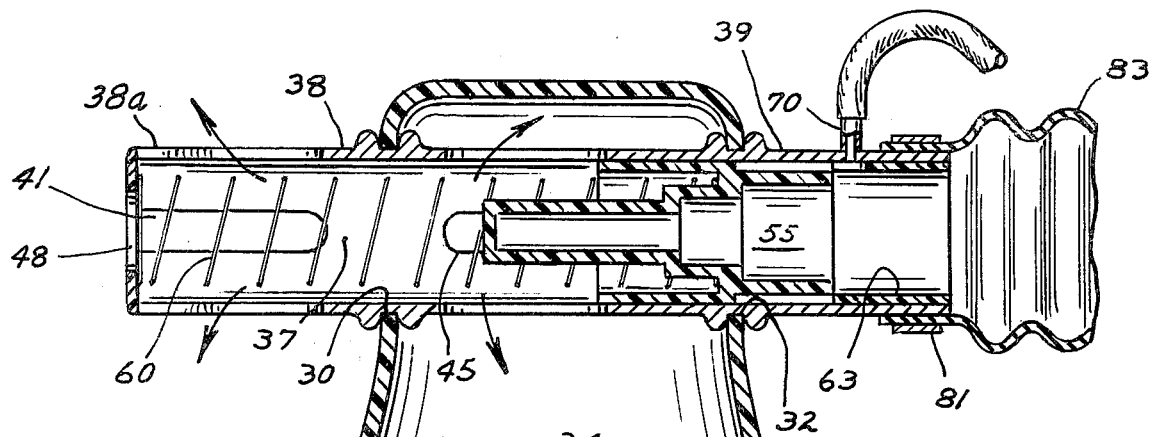
FIG. 4
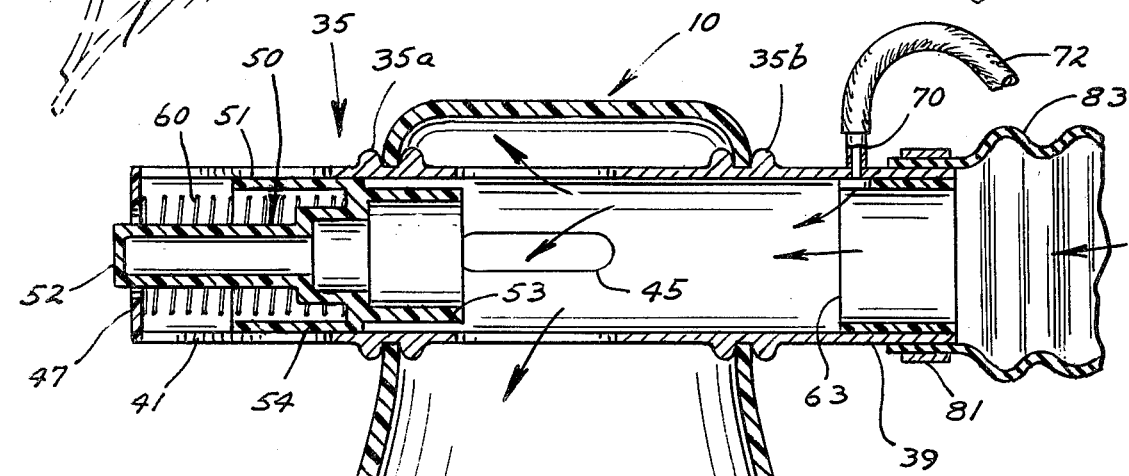
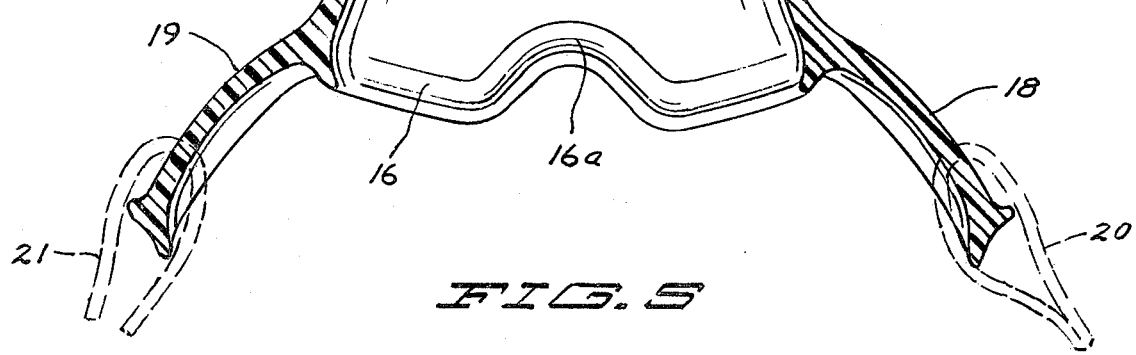
FIG. 5

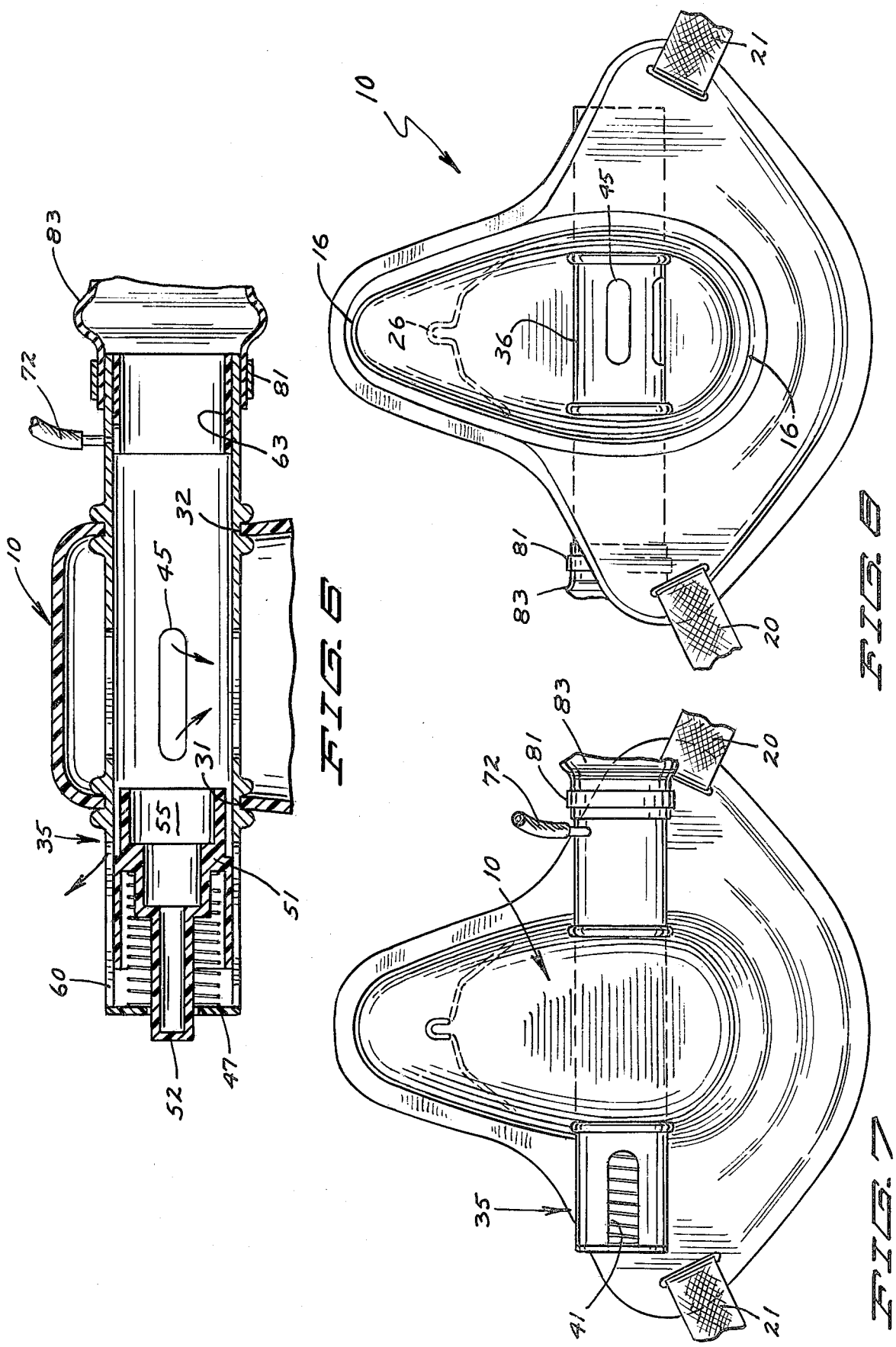

RESPIRATORY VALVE FACE MASK STRUCTURE

BACKGROUND OF THE INVENTION

1. Field of the Invention.

This invention relates to a valve equipped respiratory mask for restoration of respiration in cases of respiratory failure or cardiac arrest.

2. Description of the Prior Art.

Representative of the prior art known is the U.S. Pat. No. 3,796,216 to K. H. Schwarz wherein a flap valve serves in the alternative to close exhalation and inhalation ports with respect to a gas supply but appears to have no provision for inhalation for ambient air under atmospheric pressure and the U.S. Pat. No. 3,215,413 to J. A. Mota and No. 3,106,204 to B. Paramelle respectively disclose the use of pairs of bellows and each have a plurality of valves for inhalation, exhalation and for pressure relief purposes.

The structure herein comprising a face mask coupled with a pressurized air and oxygen supply provides a simply constructed positive acting control valve which provides pure oxygen mixed with an ambient air for a pressurized oxygen enriched air supply and which seals off communication with the atmosphere with the passage of said oxygen enriched air under pressure into the air passages of the subject.

SUMMARY OF THE INVENTION

The invention herein comprises a respiratory valve equipped oxygen mask readily adapted to be positioned air tight onto the face of a subject for the injection of oxygen enriched air to a subject suffering from respiratory failure or cardiac arrest such as in connection with the apparatus described in my pending application Ser. No. 895,733 filed Apr. 5, 1978 entitled Cardiac Pulmonary Resuscitation Apparatus.

To have effective use of the injection of oxygen enriched air into a subject there must be the cooperative relationship of a valve equipped mask readily positioned to be air tight, to suitably fit various sized faces and have a valve structure which permits free passage of ambient air under atmospheric pressure and which embodies means for simultaneously sealing off the passage of ambient air during the application of oxygen enriched air to the subject.

More specifically stated, it is an object of this invention to provide a flexible face mask having an elongated chin engaging structure with cheek flaps and an internal rib to provide an air tight fit about the air passages of a subject and which will accommodate various sized faces and integral therewith is a pressure operated switch valve which closes off ambient air when pressurized oxygen or oxygen enriched air is injected into the air passages of the subject and coupled with said valve is a relief structure to relieve an excessive build up of the pressure of oxygen or oxygen enriched air.

The above and like objects and advantages of the invention will be set forth in the following description made in connection with the accompanying drawing in which like reference characters refer to similar parts through the several views thereof.

BRIEF DESCRIPTION OF THE DRAWINGS

FIG. 1 is a broken view in side elevation showing the structure of the invention herein in an operating position;

FIGS. 2 and 3 are respective views in front and side elevation of the invention herein with portions broken away;

FIG. 4 is a view in vertical section taken on line 4—4 of FIG. 3 as indicated;

FIG. 5 is a view similar to FIG. 4 showing the structure in an alternate operating position;

FIG. 6 is a fragmentary view in section showing a detail of the valve structure in an alternate position; and FIGS. 7 and 8 are respectively top and bottom plan views with some portions broken away.

DESCRIPTION OF A PREFERRED EMBODIMENT

Referring to the drawings with particular reference to FIGS. 4 and 5, the valve equipped face mask structure comprising the invention herein is indicated generally by the reference numeral 10. The application of said mask in an operating position as indicated in FIG. 1 is with reference to my pending application Ser. No. 895,733 filed Apr. 5, 1978 entitled Cardiac Pulmonary Resuscitation Apparatus for the specific description of the supporting structure herein which shows the subject S in a supine position with its head resting on a head positioning member 7.

Said mask is designed to overlie the nose, mouth and chin facial portion of a subject, the word subject as used herein being defined as a person to whom the mask is applied as in FIG. 1.

As indicated in FIGS. 1 and 5, said mask has a perimeter 12 which will conform generally to the physical contours about the nose, mouth and chin portions of a face structure and has formed in the chin portion 14 thereof a plurality of spaced transverse grooves 15 to accommodate various lengths of faces and provide a sealing chin fit, see FIG. 2.

Said mask will be formed preferably of a suitable flexible form-retaining plastic material such as of polyvinyl chloride which plastic material has sufficient resilience to make a tight yielding fit about a face structure.

Formed on the inner surface of said mask 10 is a projecting yielding rib 16 constructed and contoured to engage and fit about the nose structure of a subject and extend just under the lower lip portion into the transverse depression thereunder and said rib is of sufficient height to form a seal when the mask is secured as will be described.

Extending or flaring outwardly of said chin portion 14 of said mask to overlie the adjacent cheek portions of the subject are flap portions 18 and 19. Said flap portions have secured thereto strap members 20 and 21 which will be secured as to an appropriate headboard such as the headboard 7 indicated in FIG. 1.

The central body portion of said mask as indicated by the reference numeral 23 projects upwardly from about said rib portion 16 and provides a chamber 24 thereunder about the nose and mouth portions or air passages of a subject.

Said rib portion 16 is arched at 16a to seat about the bridge of a nose.

Embedded in front wall 23a of said portion 23 by being moulded therein to be as shown in FIGS. 1-3 is an angled spring wire 26 which has a base portion comprising wires 26a and 26b lying along each side of a nose and being angled upwardly as at 26c arched over the bridge of the nose to form an outwardly projecting loop 26d. A strap member 27 will suitably engage said loop and pass over the head of the subject to be secured at its other end to said headboard 7 and thus will cause the upper portion of the mask 10 to seal about the nose portion of a subject. The combined holding action of said straps 20 and 21 will secure said rib 16 in a sealing position onto the lower face portion of a subject. Thus there is sealed from the atmosphere the pressurized oxygen or oxygen enriched air passing through said chamber 24 as will be further described.

Said upward projecting portion 23 is apertured as at 30 and 32, said apertures being aligned transversely thereacross to receive therethrough and to have extend outwardly thereof a cylindrical valve housing 35 which is here indicated for purpose of illustration as being formed of a plastic material and secured in position by the pairs of spaced annular ribs 35a and 35b as shown.

Said valve housing has a chamber 37 therethrough and has end portions 38 and 39 forming valve seats and having portions extending outwardly of said mask portion 24 through said apertures 30 and 32, said extended end portion 38a having a plurality of longitudinal slots or ports 41 extending thereabout and the central portion 36 of said housing has a plurality of longitudinal slots or ports 45 thereabout for communication with the air passages of the underlying nose and mouth portions of said subject.

Forming an end plate for the end portion 38 is a disc 47 having a central aperture 48 therethrough. Disposed into said housing as here shown is a cylindrical valve member 50 formed as a piston having a recessed body portion 51 having a projecting shaft or rod portion 52 passable through said aperture 48. The rear or inward body portion of said valve member is reduced in transverse dimension by here being fluted as at 53 to provide clearance with respect to adjacent wall surface of the said valve housing and the remaining forward body portion 51 of said valve member has a sealing engagement with said adjacent wall surface of said end portion 38 of said valve housing. Formed within said body portion 54 is a open ended chamber 55 facing in the direction of said valve housing end portion 39.

Disposed about said rod 52 and retained between the adjacent body of said valve member and said end plate member 47 is a coil compression spring 60 which normally urges said valve member 50 to be adjacent the end portion 39 of said valve housing to permit the free entry of ambient air through the ports or aperture 41 of said valve housing end portion 38.

Seated within the end portion 39 of said valve housing is an internal ring member 63 to form a stop or seat for said valve member 50. Carried by said end portion 39 is a projecting orificed nipple 70 with said orifice extending through said ring member 63 and providing passage into said valve housing as shown. Said nipple has secured thereto an oxygen line 72 which will run to an appropriate oxygen source 73 such as indicated in FIG. 1.

Secured to said end portion 39 by a press fit or clamp member 81 is an air hose 83 running to a pressurized air supply such as to the pump 84 indicated in FIG. 1 which is a conventional air pump with a one way air valve to pass ambient air through the hose 83.

OPERATION

The structure herein provides an effective means of supplying oxygen enriched air as required as in the case of respiratory failure or cardiac arrest. The face mask herein used in conjunction with the apparatus set forth above described is intended to place oxygen or a high level of oxygen enriched air into the lungs of a subject. It is understood that pressurized air will be supplied as required by pulmonary resuscitation.

Oxygen may be fed constantly through the hose 72 and with each stroke of the pump 84 supplying air through the line 83, the valve member 50 moves to close the ports 41 and thus delivers oxygen enriched air into the air passages of the subject. The oxygen is flowing constantly such as at two liters per minute and will accumulate to approximately 150 cc's between pump strokes and the accumulation will occur within the end portion 39 of the valve housing 35 and within the chamber 55. Said oxygen is mixed with the incoming air stroked into said valve housing through the airline 83 to provide a mixture of oxygen enriched air and the same passes through the ports 45 into the air passages of the subject as indicated in FIG. 5 and thence into the lungs at the end of each air stroke, the valve member 50 is moved directly to seat against the ring 63 and prevent suction of air from the air passage of the subject.

Said valve member 50 has its body portion 51 of such a length that when moved against the compression of the spring 60 by incoming air from the airline 83 under appropriate pressure, said valve seat will move to the point of having its body portion 54 seal off the ports 41 as indicated in FIG. 5.

The rod 52 preferably will be brightly colored and will project through the aperture 48 with each surge of incoming air to visually indicate that the air pump is operating and that air is passing into the subject's air passages. The air is suitably pumped at a pressure level such as at 150 cm of water. The spring 60 is designed to permit the closure of the ports 41 by the valve member 50 responsive to such a pressure level of incoming air.

In the event of an excessive build up of pressure of oxygen enriched air within the chamber 24 beyond the predetermined pressure limits for which purpose the spring 60 has been calibrated, the valve member will be moved further against the spring 60 and the rod 52 will extend substantially further outwardly of the end plate 47 which will be visually noted and at which point the fluted portion 53 of said valve member will have moved to underlie the slots 41 permitting the passage of oxygen or oxygen enriched air from the chamber 24 to the atmosphere to relieve the pressure within said chamber. The pressure within said chamber 24 is thus self regulating with respect to the valve member 50 according to the predetermined calibration of the spring 60 and the oxygen enriched air consumption of the subject.

The mask as indicated here is made of a flexible yielding material which conforms very nicely to different faces of subjects and the rib 16 under the pressure of the straps 20, 21 and 27 makes a very effective seal.

The spring wire member provides an outwardly projecting loop to secure one end of a strap member and further retains the form of the nose portion of the mask structure to conform very nicely to the nose of a subject.

The mask here described is a simple and safe structure and has proved to be very successful in practice. It will be understood that the mask will be used by one knowledgeable about CPR practice.

It will of course also be understood that various changes may be made in form, details, arrangement and proportions of the parts without departing from the scope of the invention herein which, generally stated, consists in an apparatus capable of carrying the objects above set forth, in the parts and combinations of parts disclosed and defined in the appended claims.

What is claimed is:

1. A respiratory valve face mask structure for use in connection with an appropriate pressurized oxygen and air supply, consisting of
   a flexible body portion formed to overlie the front portion of a face and the nose and mouth air passages of a subject,
   an internal flexible rib projecting from the underside of said body portion adapted to extend about said nose and mouth air passages of said subject and having sealing engagement with said face,
   an outward projection of said body portion from said rib forming a chamber,
   a valve having a central portion disposed through said projecting portion and said chamber a first end portion and a second end portion each extending outwardly of said projecting portion, said first and second end portions and said central portion having a passage therethrough,
   first air ports disposed longitudinally of said central portion of said housing and communicating said chamber with said passages,
   said first end portion of said valve housing having second air ports communicating with the atmosphere, said first and portion having a portion thereof forming a first valve seat between said first and second air ports
   a pressurized oxygen supply and a pressurized air supply connected to said second end portion of said housing,
   said second end portion of said valve housing forming a second valve seat between said pressurized oxygen supply and pressurized air supply and said first air ports,
   a valve member slidably disposed within said passage of said housing and being movable to first, second and third positions,
   means normally urging said valve member to said first position to engage said second valve seat to seal said air ports from said pressurized oxygen and air supply and to admit the passage of ambient air,
   said urging means yielding to a first predetermined pressure of incoming pressurized air from said air supply bearing against said valve member to said second position for movement of said valve member to engage said first valve seat to seal off the entry of ambient air and pass said pressurized air to said air passages,
   said urging means yielding further to a second higher degree of pressure of air within said chamber for movement of said member to said third position communicating said second air ports with said passage.

2. The structure set forth in claim 1, wherein
   said first end portion of said valve housing has said second air ports thereabout and an aperture in an end wall thereof passing ambient air through said first valve seat into said passage of said housing when said valve member is in its first position,
   said valve member has a projecting rod extending therefrom and passing through said aperture of said end wall when said valve member is in its second and third positions,
   said urging means comprises a compression spring disposed about said rod and bearing against said valve member and against said end wall of said first end portion of said valve housing,
   said spring normally urges said valve member into said second valve seat,
   means in said second end portion of said valve housing forming a stop member for said valve member, and
   said valve member and said spring yield to the pressure of incoming pressurized air from said pressurized air supply and said rod extends through said aperture indicating the presence of pressurized air passing into said valve housing.

3. The structure set forth in claim 2, wherein
   said valve member has an end portion of reduced transverse dimension remote from said projecting rod.
   said valve member and said compression spring yield under said second higher degree of pressure of said pressurized incoming air in said valve housing for further movement of said valve member toward said first end portion of said valve housing for further projection of said rod through said aperture of said end wall and for said portion of reduced dimension of said valve member to be moved to underlie said second air ports of said first end portion to relieve said second higher degree of air pressure to the atmosphere, and
   said rod is color coded for clear visual indication that said last mentioned pressure is being relieved.

4. The structure set forth in claim 3, wherein said end portion of reduced transverse dimension of said valve member is fluted.

5. The structure set fourth in claim 1, wherein
   said valve member is substantially cylindrical in form having an open ended chamber formed therein facing said second end portion of said valve housing,
   said second end portion of said valve housing has an orifice therein,
   means connecting said orifice with a pressurized supply of oxygen passing into said second end portion of said valve housing and said oxygen accumulates within said chamber of said valve member.

6. The structure set forth in claim 1, wherein
   said second end portion of said valve housing has an orificed nipple,
   means connecting said nipple with a pressurized supply of oxygen,
   means connecting said second end portion of said valve housing with a pressurized supply of air,
   said valve member has an open ended chamber formed therein thereof facing said second end portion of said valve housing, and
   said nipple passes said oxygen into said valve housing and the same accumulates therein and within said chamber of said valve member whereby when said pressurized air is passed into said valve housing, said valve member moves in the direction of said first end portion of said valve housing to seal the same and said incoming air passes through said second valve seat and mixes with said accumulated oxygen within said valve housing to pass oxygen enriched air into said chamber.

7. The structure set forth in claim 1, wherein
   said first end portion of said valve housing has an outer end wall having an aperture therethrough,
   said valve member has a rod projecting in the direction of said first end portion of said valve housing and adapted to pass through said aperture, whereby the projection of said rod through said apertures indicates the passage of pressurized air into said valve housing.

8. The structure set forth in claim 1, wherein said body portion has a pair of laterally extending flap portions adapted to overly either side of said face portion, fastening means in connection with each of said flap portions, and fastening means extending from said outwardly projecting portion whereby said first and second mentioned fastening means cooperate to secure said mask about the head of said subject.

9. The structure set forth in claim 1, including resilient means embedded within said outwardly projecting portion conforming the same to the form of a nose.

* * * * *